(12) United States Patent
Elia et al.

(10) Patent No.: US 7,737,313 B2
(45) Date of Patent: Jun. 15, 2010

(54) CATALYST COMPOSITION, THE METHOD OF MANUFACTURING, AND THE PROCESS OF USING THEREOF IN HYDROCARBON CONVERSIONS

(75) Inventors: Christine N. Elia, Bridgewater, NJ (US); Frederick Y. Lo, Middlesex, NJ (US); Michael C. Clark, Pasadena, TX (US); C. Morris Smith, West University Place, TX (US); Michael Hryniszak, Bordentown, NJ (US); Mohan Kalyanaraman, Media, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 573 days.

(21) Appl. No.: 11/643,550

(22) Filed: Dec. 21, 2006

(65) Prior Publication Data

US 2008/0154081 A1   Jun. 26, 2008

(51) Int. Cl.
   *C07C 2/66* (2006.01)
(52) U.S. Cl. .................. 585/467; 585/470; 585/471
(58) Field of Classification Search ............ 585/467, 585/470, 471
   See application file for complete search history.

(56) References Cited

U.S. PATENT DOCUMENTS

| | | | |
|---|---|---|---|
| 4,891,458 A | 1/1990 | Innes et al. | |
| 4,954,325 A | 9/1990 | Rubin et al. | |
| 4,992,606 A | 2/1991 | Kushnerick et al. | |
| 5,334,795 A | 8/1994 | Chu et al. | |
| 5,493,065 A | 2/1996 | Cheng et al. | |
| 6,034,291 A | 3/2000 | Girotti et al. | |
| 6,835,862 B1 * | 12/2004 | Gajda et al. | 585/467 |
| 6,858,129 B2 * | 2/2005 | Mohr et al. | 208/120.01 |
| 6,919,491 B1 | 7/2005 | Cheng et al. | |
| 2003/0121827 A1 * | 7/2003 | van den Berge et al. | 208/120.01 |

FOREIGN PATENT DOCUMENTS

| | | |
|---|---|---|
| WO | 98/14417 | 4/1998 |
| WO | 2004/052810 | 6/2004 |
| WO | 2004/056475 | 7/2004 |
| WO | 2006/002805 | 1/2006 |

OTHER PUBLICATIONS

Corma et al., Alkylation of Benzene with Short-Chain Olefins over MCM-22 Zeolite: Catalytic Behavior and Kinetic Mechanism, Journal of Catalysis, 192, pp. 163-173, (2000), no month available.*
A. Corma et al., "*Synthesis and Characterization of the MCM-22 Zeolite*", Zeolites 15:2-8, 1995.

* cited by examiner

*Primary Examiner*—Elizabeth D Wood
(74) *Attorney, Agent, or Firm*—D. M. Tyus; Xiaobing Feng (57) ABSTRACT

A catalyst composition comprises (a) a MCM-22 family molecular sieve; and (b) a binder, wherein the MCM-22 family molecular sieve is characterized by an average crystal agglomerate size of less than or equal to 16 microns. The catalyst composition may further have a second molecular sieve having a Constraint Index of less than 12, e.g., less than 2. Examples of molecular sieve useful for this disclosure are a MCM-22 family molecular sieve, zeolite Y, and zeolite Beta. The catalyst composition may be used for the process of alkylation or transalkylation of an alkylatable aromatic compound with an alkylating agent.

13 Claims, 2 Drawing Sheets

CATALYST COMPOSITION, THE METHOD OF MANUFACTURING, AND THE PROCESS OF USING THEREOF IN HYDROCARBON CONVERSIONS

FIELD

This invention relates to a novel catalyst composition, the method of manufacturing, and the process of using thereof for hydrocarbon conversions. In particular, the novel catalyst composition of this disclosure comprises a molecular sieve and a binder, wherein the MCM-22 family molecular sieve is characterized by an average crystal agglomerate size of less than or equal to 16 microns. The hydrocarbon conversions comprise alkylation and/or transalkylation of alkylatable aromatics.

BACKGROUND OF THIS DISCLOSURE

The alkylation of aromatic hydrocarbon compounds employing zeolite catalysts is known and understood in the art. U.S. Pat. No. 5,334,795 describes the liquid phase alkylation of benzene with ethylene in the presence of MCM-22 to produce ethylbenzene; and U.S. Pat. No. 4,891,458 discloses liquid phase alkylation and transalkylation processes using zeolite beta.

Zeolite-based catalysts are used in the alkylation of benzene with propylene to produce cumene. U.S. Pat. No. 4,992,606 discloses a process for preparing cumene using MCM-22 in liquid phase.

The alkylation of benzene with ethylene and propylene to form ethylbenzene (EB) and cumene respectively produce the desired monoalkylated compound along with undesired polyalkylated impurities by contacting an alkylatable aromatic compound and an alkylating agent in the presence of a catalyst. Therefore, there is a need for novel catalyst composition and the process of using such catalyst composition in the alkylation and/or transalkylation processes that increase the selectivity to the desired monoalkylated aromatic compound at equivalent activity. This disclosure meets this and other needs.

SUMMARY OF THIS DISCLOSURE

In some embodiments, this disclosure relates to a catalyst composition comprising:
(a) a MCM-22 family molecular sieve; and
(b) a binder,
wherein the MCM-22 family molecular sieve is characterized by an average crystal agglomerate size of less than or equal to 16 microns, preferably less than or equal to 15 microns, more preferably less than or equal to 10 microns, even more preferably less than or equal to 5 microns, and most preferably less than or equal to 2 microns.

In other embodiments, this disclosure relates to a process for alkylation or transalkylation of an alkylatable aromatic compound with an alkylating agent to produce a monoalkylated aromatic compound, comprising the steps of:
(a) contacting at least one alkylatable aromatic compound and at least one alkylating agent with a catalyst composition under suitable alkylation or transalkylation conditions, to produce at least one effluent which comprises the monoalkylated aromatic compound, the catalyst composition having a monoalkylated aromatic compound selectivity; the catalyst composition comprising:
(i) a MCM-22 family molecular sieve; and
(ii) a binder,
wherein the MCM-22 family molecular sieve is characterized by an average crystal agglomerate size of less than or equal to 16 microns, preferably less than or equal to 15 microns, more preferably less than or equal to 10 microns, even more preferably less than or equal to 5 microns, and most preferably less than or equal to 2 microns,
wherein the monoalkylated aromatic compound selectivity of the catalyst composition is greater than the monoalkylated aromatic compound selectivity of a catalyst composition having an average crystal agglomerate size greater than 16 microns, when the reaction zone is operated under equivalent conditions.

In some embodiments, the monoalkylated aromatic compound selectivity of the catalyst composition of this disclosure is 10%, preferably 20%, more preferably 30%, even more preferably 40%, yet even more preferably 50%, and most preferably 60%, greater than the monoalkylated aromatic compound selectivity of a catalyst composition having an average crystal agglomerate size greater than 16 microns, when the reaction zone is operated under equivalent conditions.

In one aspect, the MCM-22 family molecular sieve comprises at least one of MCM-22, MCM-36, MCM-49, MCM-56, ITQ-1, ITQ-30, and any combination thereof. In another aspect, the binder comprises at least one of a titanium compound, an alumina compound, a silicon compound, or any mixture thereof. In a preferred embodiment, the binder is selected from a group consisting of silica, alumina, zirconia, titania, thoria, beryllia, magnesia, silica-alumina, silica-magnesia, silica-zirconia, silica-thoria, silica-beryllia, silica-titania, silica-alumina-thoria, silica-alumina-zirconia, silica-alumina-magnesia, silica-magnesia-zirconia, and any combination thereof. In another preferred embodiment, the catalyst composition has at least 1 wt %, preferably at least 10 wt %, more preferably at least 50 wt %, even more preferably at least 60 wt %, at least 65 wt %, at least 70 wt %, at least 75 wt %, and most preferably at least 80 wt %, of the MCM-22 family molecular sieve based on the total weight of the catalyst composition.

In one embodiment, the catalyst composition further comprises a second molecular sieve having a Constraint Index of less than 12. In another embodiment, the catalyst composition further comprises a second molecular sieve having a Constraint Index of less than 2.

In a preferred embodiment, the average crystal agglomerate size MCM-22 family molecular sieve is reduced by any physical or chemical means, for example, by crashing, milling, grinding, jet milling, slurry/spray drying, pressing, mixing, or any combination thereof, to the desired average crystal agglomerate size, wherein the desired average crystal agglomerate size is less than or equal to 16 microns, preferably less than or equal to 15 microns, more preferably less than or equal to 10 microns, even more preferably less than or equal to 5 microns, and most preferably less than or equal to 2 microns.

In one embodiment, the process for alkylation or transalkylation of an alkylatable aromatic compound with an alkylating agent to produce a monoalkylated aromatic compound further comprises a finishing reactor downstream of the reaction zone.

In one aspect, the suitable alkylation or transalkylation conditions include a temperature from about 100° C. to about 400° C., a pressure from about 20.3 to 4500 kPa-a, a WHSV from about 0.1 to about 10 hr$^{-1}$, and a molar ratio of the alkylatable compound over the alkylating agent from about 0.1:1 to 50:1.

In a preferred embodiment, the monoalkylated aromatic compound comprises ethylbenzene, the alkylatable aromatic compound comprises benzene, and the alkylating agent comprises ethylene. In yet another preferred embodiment, the monoalkylated aromatic compound comprises cumene, the alkylatable aromatic compound comprises benzene, and the alkylating agent comprises propylene.

In some embodiments, this disclosure relates to a process for preparing the catalyst composition of this disclosure comprising:

(a) providing the MCM-22 family molecular sieve having an average crystal agglomerate size of less than or equal to 16 microns and the binder to form a mixture; and (b) forming the mixture into the catalyst composition.

In one aspect, the forming step comprises extruding. In another aspect, the catalyst composition has a shape of quadrulobe. In a preferred embodiment, the catalyst composition has at least 1 wt %, preferably at least 10 wt %, more preferably at least 50 wt %, even more preferably at least 60 wt %, at least 65 wt %, at least 70 wt %, at least 75 wt %, and most preferably at least 80 wt %, of crystalline MCM-22 family molecular sieve based on the total weight of the catalyst composition. In yet another preferred embodiment, the catalyst composition further at least 5 wt % of a molecular sieve having a *BEA framework type based on the total weight of the catalyst composition.

In a preferred embodiment, the process or preparing the catalyst composition further comprises a step of milling, e.g., jet-milling, a MCM-22 family molecular sieve to form the MCM-22 family molecular sieve having an average crystal agglomerate size of less than or equal to 16 microns.

DETAILED DESCRIPTION OF THIS DISCLOSURE

Introduction

All patents, patent applications, test procedures, priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated.

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

The term "MCM-22 family material" (or "material of the MCM-22 family" or "molecular sieve of the MCM-22 family"), as used herein, includes:

(i) molecular sieves made from a common first degree crystalline building block "unit cell having the MWW framework topology". A unit cell is a spatial arrangement of atoms which is tiled in three-dimensional space to describe the crystal as described in the "Atlas of Zeolite Framework Types", Fifth edition, 2001, the entire content of which is incorporated as reference;

(ii) molecular sieves made from a common second degree building block, a 2-dimensional tiling of such MWW framework type unit cells, forming a "monolayer of one unit cell thickness", preferably one c-unit cell thickness;

(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, and any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575) and MCM-56 (described in U.S. Pat. No. 5,362,697). The entire contents of the patents are incorporated herein by reference.

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of the molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstroms.

As used herein, an "alkylatable aromatic compound" is a compound that may receive an alkyl group and an "alkylating agent" is a compound which may donate an alkyl group to an alkylatable aromatic compound. One example of the alkylatable aromatic compounds is benzene. Examples of the alkylating agent are ethylene, propylene, polyalkylated aromatic compound(s), e.g., di-ethylbenzene, tri-ethylbenzene, di-isopropylbenzene, and tri-isopropylbenzene The term "wppm" as used herein is defined as parts per million by weight.

The term "average crystal agglomerate" as used herein, means the arithmetic average of the diameter distribution of the particles on a volume basis. The average crystal agglomerate may be measured by using Scan Electron Microscopy (SEM) technology.

The term "equivalent alkylation or transalkylation conditions" or "equivalent conditions" as used herein, means that reaction conditions such as the feed composition, the amount of catalyst charge (weight), the reaction temperature, the reaction pressure, and the space hourly velocity are the same.

The term "aromatic" as used herein is to be understood in accordance with its art-recognized scope which includes alkyl substituted and unsubstituted mono- and polynuclear compounds. Compounds of an aromatic character, which possess a heteroatom, are also useful provided sufficient activity can be achieved if they act as catalyst poisons under the reaction conditions selected.

Catalyst

The catalyst composition of this disclosure comprises a molecular sieve and a binder, wherein the MCM-22 family molecular sieve is characterized by an average crystal agglomerate size of less than or equal to 16 microns, preferably less than or equal to 15 microns, more preferably less than or equal to 10 microns, even more preferably less than or equal to 5 microns, and most preferably less than or equal to 2 microns. In a preferred embodiment, the average crystal agglomerate size MCM-22 family molecular sieve is reduced by any physical or chemical means, for example, by crashing, milling, grinding, jet milling, slurry/spray drying, pressing, mixing, or any combination thereof, to the desired average crystal agglomerate size, wherein the desired average crystal agglomerate size is less than or equal to 16 microns, preferably less than or equal to 15 microns, more preferably less than or equal to 10 microns, even more preferably less than or equal to 5 microns, and most preferably less than or equal to 2 microns.

In some embodiments, the molecular sieve of the catalyst composition further comprises a medium pore molecular sieve having a Constraint Index of 2-12 and/or a large pore molecular sieve having a Constraint Index of less than 2. In one embodiment, the molecular sieve has a framework type of at least one of FAU, *BEA, MFI, MTW, MWW, and any combination thereof.

In some embodiments, the molecular sieve of this disclosure comprises a crystalline MCM-22 family molecular sieve. In other embodiments, the molecular sieve of this disclosure comprises at least one of MCM-22, MCM-49, MCM-56, ITQ-1, ITQ-30, an intergrowth-phase thereof, or a mix phase thereof. In a preferred embodiment of this disclosure, the catalyst composition of this disclosure has at least 1 wt %, preferably at least 10 wt %, more preferably at least 50 wt %, even more preferably at least 60 wt %, at least 65 wt %, at least 70 wt %, at least 75 wt %, and most preferably at least 80 wt %, of the crystalline MCM-22 family molecular sieve based on the total weight of the catalyst composition. In yet another preferred embodiment of this disclosure, the catalyst composition of this disclosure has at least 1 wt %, preferably at least 10 wt %, more preferably at least 50 wt %, even more preferably at least 60 wt %, at least 65 wt %, at least 70 wt %, at least 75 wt %, and most preferably at least 80 wt %, of MCM-22, MCM-49, MCM-56, and/or any combination thereof based on the total weight of the catalyst composition.

The crystalline MCM-22 family molecular sieve of this disclosure may contain less than 10 weight percent (wt %), preferably less than 5 wt %, even more preferably less than 1 wt %, of non-MCM-22 family molecular sieve(s) based on the total weight of the crystalline molecular sieve composition. Typical examples of the non-MCM-22 family molecular sieve(s) co-existing with the MCM-22 family molecular sieve(s) of this disclosure are Kenyaite, EU-1, ZSM-50, ZSM-12, ZSM-48, ZSM-5, Ferrierite, Mordenite, Sodalite, and/or Analcine. Other examples of the non-MCM-22 family molecular sieve(s) co-existing with the MCM-22 family molecular sieve(s) of this disclosure are molecular sieves having framework type of EUO, MTW, FER, MOR, SOD, ANA, and/or MFI. The product of the synthesis may comprises less than 10 wt %, preferably less than 5 wt %, even more preferably less than 1 wt %, of non-crystalline materials, e.g., quartz, based on the total weight of the crystalline molecular sieve composition.

In some embodiments, the catalyst composition further comprises at least 1 wt %, preferably at least 5 wt %, of a molecular sieve having a Constraint Index of 2-12 or a Constraint Index of less than 2. In a preferred embodiments, the catalyst composition further comprises at least 1 wt %, preferably at least 5 wt %, of a molecular sieve having a *BEA framework type based on the total weight of the catalyst composition.

Suitable medium pore molecular sieves having a Constraint Index of 2-12 (as defined in U.S. Pat. No. 4,016,218), include ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-1 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. The entire contents of all the above patent specifications are incorporated herein by reference.

Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. The entire contents of all the above patent specifications are incorporated herein by reference.

The Constraint Index is a convenient measure of the extent to which an aluminosilicate or molecular sieve provides controlled access to molecules of varying sizes to its internal structure. For example, aluminosilicates which provide a highly restricted access to and egress from its internal structure have a high value for the constraint index, and aluminosilicates of this kind usually have pores of small size, e.g. less than 5 Angstroms. On the other hand, aluminosilicates which provide relatively free access to the internal aluminosilicate structure have a low value for the constraint index, and usually pores of large size. The method by which Constraint Index may be determined is described fully in U.S. Pat. No. 4,016,218, which is incorporated herein by reference.

It will be understood by a person skilled in the art that the crystalline MCM-22 family material may contain impurities, such as amorphous materials; unit cells having non-MWW framework topologies (e.g., MFI, MTW); and/or other impurities (e.g., heavy metals and/or organic hydrocarbons). The crystalline MCM-22 family materials of this disclosure are preferably substantially free of non-MCM-22 family material (s). The term "substantially free of non-MCM-22 family material(s)" used herein means the crystalline MCM-22 family material of this disclosure preferably contains a minor proportion (less than 50 wt %), preferably less than 20 wt %, more preferably less than 10 wt %, even more preferably less than 5 wt %, and most preferably less than 1 wt %, of non-MCM-22 family materials ("impurities") in the crystalline MCM-22 family materials, which wt % values are based on the combined weight of impurities and pure phase crystalline MCM-22 family materials.

The MCM-22 crystalline material has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, the material has a formula, on an anhydrous basis and in terms of moles of oxides per n moles of $YO_2$, as follows:

$$(0.005\text{-}1)M_2O:(1\text{-}4)R:X_2O_3:nYO_2$$

wherein M is an alkali or alkaline earth metal, and R is an organic moiety. The M and R components are associated with the material as a result of their presence during synthesis, and are typically removed by post-synthesis methods well known to those skilled in the art and/or hereinafter more particularly described.

To the extent desired, the original metal cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups 1-17, preferably Groups 2-12 of the Periodic Table of the Elements.

The stability of the catalyst(s) used in the present process may be increased by steaming. U.S. Pat. Nos. 4,663,492; 4,594,146; 4,522,929; and 4,429,176, describe conditions for the steam stabilization of zeolite catalysts which may be utilized to steam-stabilize the catalyst. Reference is made to these patents for a detailed description of the steam stabilization technique for use with the present catalysts. The steam stabilization conditions typically include contacting the catalyst with, e.g., 5-100% steam at a temperature of at least about 300° C. (e.g., 300°-650° C.) for at least one hour (e.g., 1-200 hours) at a pressure of 101-2,500 kPa-a. In a more particular embodiment, the catalyst may be made to undergo steaming with 75-100% steam at 315°-500° C. and atmospheric pressure for 2-25 hours. The steaming of the catalyst may take place under conditions sufficient to initially increase the Alpha Value of the catalyst, the significance of which is discussed below, and produce a steamed catalyst having an enhanced Alpha Value. If desired, steaming may be continued to subsequently reduce the Alpha Value from the higher Alpha Value to an Alpha Value which is substantially the same as the Alpha Value of the unsteamed catalyst.

In some aspects of this disclosure, the binder of the catalyst composition of this disclosure comprises at least one of an aluminum compound, a titanium compound, a silicon compound, and any combination thereof. In some embodiments, the aluminum compound comprises at least one of aluminum oxide, aluminum hydroxide, aluminum sulfate, aluminum phosphate, and any combination thereof. Preferably, the catalyst composition has at least 1 wt % of the binder based on the total weight of the catalyst composition.

In yet other embodiments, this disclosure relates to a process for preparing the catalyst composition of this disclosure, the process comprises (a) providing the molecular sieve and the binder to form a mixture; and (b) forming the mixture into the catalyst composition. The crystals prepared by the instant invention can be shaped into a wide variety of particle sizes. Generally, the particles can be in the form of a powder, a granule, or a molded product, such as an extrudate. In cases where the catalyst is molded, such as by extrusion, the crystals can be extruded before drying or partially dried and then extruded. In a preferred embodiment, the forming step comprises extruding. In another preferred embodiment, the catalyst composition has a shape of quadrulobe. In one embodiment, the catalyst composition has at least 50 wt %, preferably at least 65 wt % of at least one of MCM-22, MCM-49, MCM-56, and MCM-36 based on the total weight of the catalyst composition.

In some embodiments, the catalyst composition may further comprise a material resistant to the temperatures and other conditions employed in organic conversion processes. Such materials include clays, silica and/or metal oxides such as alumina. The latter may be either naturally occurring or in the form of gelatinous precipitates or gels including mixtures of silica and metal oxides. These materials may be incorporated into naturally occurring clays, e.g., bentonite and kaolin, to improve the crush strength of the catalyst under commercial operating conditions. The materials, i.e. clays, oxides, etc., function as binders for the catalyst. It is desirable to provide a catalyst having good crush strength because in commercial use it is desirable to prevent the catalyst from breaking down into powder-like materials.

Naturally occurring clays which can be composited with the crystalline molecular sieve include the montmorillonite and kaolin family, which families include the subbentonites, and the kaolins commonly known as Dixie, McNamee, Georgia and Florida clays or others in which the main mineral constituent is halloysite, kaolinite, dictite, narcite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the crystalline molecular sieve can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline molecular sieve and inorganic oxide matrix vary widely, with the crystal content ranging from about 1 to about 99 percent by weight and more usually, particularly when the composite is prepared in the form of beads, in the range of about 20 to about 80 wt % of the composite.

A summary of the molecular sieves and/or zeolites, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known forming techniques, like spray drying, prilling, pelletizing and extrusion, have been and are being used to produce macrostructures in the form of, for example, spherical particles, extrudates, pellets and Tablets of both micropores and other types of porous materials for use in catalysis, adsorption and ion exchange. A summary of these techniques is described in "Catalyst Manufacture," A. B. Stiles and T. A. Koch, Marcel Dekker, New York, 1995.

Alkylation Reactions

In another embodiment, this disclosure discloses a process for alkylating an aromatic hydrocarbon with an alkylating agent to produce an alkylated aromatic product, the process comprises contacting the aromatic hydrocarbon and the alkylating agent with the catalyst composition under alkylation conditions effective to alkylate the aromatic hydrocarbon with the alkylating agent to form an effluent comprising the alkylated aromatic product. In some preferred embodiments, the aromatic hydrocarbon comprises benzene, the alkylating agent comprises ethylene, and the alkylated aromatic product comprises ethylbenzene. In other preferred embodiments, the aromatic hydrocarbon comprises benzene, the alkylating agent comprises propylene, and the alkylated aromatic product comprises cumene.

The crystalline MCM-22 family molecular sieve(s) of this disclosure are also useful catalyst for transalkylations, such as, for example, polyalkylbenzene transalkylations.

Substituted aromatic compounds which may be used for the invention should possess at least one hydrogen atom directly bonded to the aromatic nucleus. The aromatic rings may be substituted with one or more alkyl, aryl, alkaryl, alkoxy, aryloxy, cycloalkyl, halide, and/or other groups which do not interfere with the alkylation reaction.

Suitable aromatic compounds that may be used for this invention include benzene, naphthalene, anthracene, naphthacene, perylene, coronene, and phenanthrene, with benzene being preferred.

Suitable alkyl substituted aromatic compounds that may be used for this invention include toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate streams that may contain substantial quantities of benzene, toluene and/or xylene may be particularly suitable feed for the process of this invention. Although the process is particularly directed to the production of ethylbenzene from polymer grade and dilute ethylene, it is equally applicable to the production of other $C_7$-$C_{20}$ alkylaromatic compounds, such as cumene, as well as $C_6$+ alkylaromatics, such as $C_8$-$C_{16}$ linear and near linear alkylbenzenes.

Suitable alkylating agent(s) that may be used in this disclosure comprise alkene compound(s), alcohol compound(s), and/or alkylbenzene(s), and mixtures thereof. Other suitable alkylating agents that may be useful in the process of this disclosure generally include any aliphatic or aromatic organic compound having one or more available alkylating aliphatic groups capable of reaction with the alkylatable aromatic compound. Examples of suitable alkylating agents are $C_2$-$C_{16}$ olefins such as $C_2$-$C_5$ olefins, viz., ethylene, propylene, the butenes, and the pentenes; $C_1$-$C_{12}$ alkanols (inclusive of monoalcohols, dialcohols, trialcohols, etc.), preferably $C_1$-$C_5$ alkanols, such as methanol, ethanol, the propanols, the butanols, and the pentanols; $C_2$-$C_{20}$ ethers, e.g., $C_2$-$C_5$ ethers including dimethylether and diethylether; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, polyalkylated aromatic compound(s), e.g., bi-alkylated benzenes (e.g., bi-ethylbenzene(s) or bi-isopropylbenzenes) and tri-alkylated benzene(s) (e.g., tri-ethylbenzenes or tri-isopropylbenzenes), and so forth. Thus the alkylating agent may preferably be selected from the group consisting of $C_2$-$C_5$ olefins, $C_1$-$C_5$ alkanols, bi-ethylbenzene(s), bi-isopropylbenzene(s), tri-ethylbenzene(s) and/or tri-isopropylbenzene(s). The alkylating agent includes a concentrated alkene feedstock (e.g., polymer grade olefins) and a dilute alkene feedstock (e.g., catalytic cracking off-gas).

Suitable alkyl substituted aromatic compounds which may be prepared from the alkylation process of the present invention include toluene, xylene, isopropylbenzene (cumene), normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m- xylene; dimethylnaphthalenes; ethylnaphthalene; 2,3-dimethyl,anthracene; 9-ethylanthracene; 2-methylanthracene; o-methylanthracene; 9,10-dimethylphenanthrene; and 3-methyl-phenanthrene. Preferably, the alkylated aromatic product comprises monoalkylbenzene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often alkylate is obtained as a high boiling fraction in which the alkyl group attached to the aromatic nucleus varies in size from about $C_6$ to about $C_{16}$.

The alkylation reaction is carried out with the alkylatable aromatic compound and the alkylating agent in the reaction zone under alkylation or transalkylation conditions. The alkylation or transalkylation conditions include a temperature of 100 to 285° C. and a pressure of 689 to 4601 kPa-a, preferably, a pressure of 1500 to 3000 kPa-a, a WHSV based on alkylating agent (e.g., alkene) for overall reactor of 0.1 to 10 $hr^{-1}$, preferably, 0.2 to 2 $hr^{-1}$, more preferably, 0.5 to 1 $hr^{-1}$, or a WHSV based on both alkylating agent and alkylatable aromatics for overall reactor of 10 to 100 $hr^{-1}$, preferably, 20 to 50 $hr^{-1}$. The alkylatable aromatic compound is alkylated with the alkylating agent (e.g., alkene) in the presence of an alkylation or transalkylation catalyst in a reaction zone or a plurality of reaction zones. The reaction zone(s) are preferably located in a single reactor vessel, but may include another reaction zone having an alkylation or transalkylation catalyst bed, located in separate vessel which may be a by-passable and which may operate as a reactive guard bed. The catalyst composition used in the reactive guard bed may be different from the catalyst composition used in the reaction zone. The catalyst composition used in the reactive guard bed may have multiple catalyst compositions. At least one reaction zone, and normally each reaction zone, is maintained under conditions effective to cause alkylation of the alkylatable aromatic compound with the alkylating agent in the presence of an alkylation or transalkylation catalyst.

The effluent from the reaction zone comprises the desired alkylated aromatic product, unreacted alkylatable aromatic compound, any unreacted alkylating agent (e.g., alkene, alkene conversion is expected to be at least 90 mol. %, preferably, about 98-99.9999 mol. %) and the alkane component and the other impurities. In one embodiment, at least a portion of the effluent is fed to another reaction zone where an alkylating agent is added for reaction with the unreacted alkylatable aromatic compound with an alkylation or transalkylation catalyst. Furthermore, at least a portion the effluent from any of the reaction zone(s) may be fed directly or indirectly to a transalkylation unit.

In addition to, and upstream of, the reaction zones, a by-passable reactive or unreactive guard bed may normally be located in a reactor separate from the alkylation reactor. Such guard bed may also be loaded with an alkylation or transalkylation catalyst, which may be the same or different from the catalyst used in the reaction zone(s). Such guard bed is maintained from under ambient conditions, or at suitable alkylation or transalkylation conditions. At least a portion of alkylatable aromatic compound, and optionally at least a portion of the alkylating agent, are passed through the unreactive or reactive guard bed prior to entry into the reaction zone. These guard beds not only serve to affect the desired alkylation reaction, but is also used to remove any reactive impurities in the feeds, such as nitrogen compounds, which could otherwise poison the remainder of the alkylation or transalkylation catalyst. The catalyst in the reactive or unreactive guard bed is therefore subject to more frequent regeneration and/or replacement than the remainder of the alkylation or transalkylation catalyst, and hence the guard bed is typically provided with a by-pass circuit so that the alkylation feed(s) may be fed directly to the series connected reaction zones in the reactor while the guard bed is out of service. The reactive or unreactive guard bed may be operated in co-current upflow or downflow operation.

The reaction zone(s) used in the process of the present invention is typically operated so as to achieve essentially complete conversion of the alkene. However, for some applications, it may be desirable to operate at below 100% alkene conversion. The employment of a separate finishing reactor downstream of the reaction zone(s) may be desirable under certain conditions. The finishing reactor would also contain alkylation or transalkylation catalyst, which could be the same or different from the catalyst used in other reaction zones in the alkylation or transalkylation reactor(s) and may be maintained under at least partially liquid phase or alternately vapor phase alkylation or transalkylation conditions. The polyalkylated aromatic compounds in the effluents may be separated for transalkylation with alkylatable aromatic compound(s). The alkylated aromatic compound is made by transalkylation between polyalkylated aromatic compounds and the alkylatable aromatic compound.

The alkylation or transalkylation reactor(s) used in the process of the present invention may be highly selective to the desired monoalkylated product, such as ethylbenzene, but typically produces at least some polyalkylated species. In one embodiment, the effluent from the final alkylation reaction zone is subjected to a separation step to recover polyalkylated aromatic compound(s). In another embodiment, at least a portion of the polyalkylated aromatic compound is supplied to a transalkylation reactor which may be separate from the alkylation reactor. The transalkylation reactor produces an effluent which contains additional monoalkylated product by reacting the polyalkylated species with an alkylatable aromatic compound. At least a portion of these effluents may be separated to recover the alkylated aromatic compound (monoalkylated aromatic compound and/or polyalkylated aromatic compound).

Particular conditions for carrying out the alkylation of benzene with ethylene at least partially in liquid phase may have a temperature of from about 120 to 285° C., preferably, a temperature of from about 150 to 260° C., a pressure of 689 to 4601 kPa-a, preferably, a pressure of 1500 to 4137 kPa-a, a WHSV based on total ethylene and total catalyst for overall reactor of 0.1 to 10 $hr^{-1}$, preferably, 0.2 to 2 $hr^{-1}$, more preferably, 0.5 to 1 $hr^{-1}$, or a WHSV based on both total ethylene and benzene, and total catalyst for overall reactor of 10 to 100 $hr^{-1}$, preferably, 20 to 50 $hr^{-1}$, and a molar ratio of benzene to ethylene from about 1 to about 10.

Particular conditions for carrying out the at least partially in liquid phase alkylation of benzene with propylene may include a temperature of from about 80 to 160° C., a pressure of about 680 to about 4800 kPa-a; preferably from about 100 to 140° C. and pressure of about 2000 to 3000 kPa-a, a WHSV based on propylene of from about 0.1 about 10 $hr^{-1}$, and a molar ratio of benzene to ethylene from about 1 to about 10.

Where the alkylation system includes a reactive guard bed, it is maintained under at least partial in liquid phase conditions. The guard bed will preferably operate at a temperature of from about 120 to 285° C., a temperature of from about 150 to 260° C., a pressure of 689 to 4601 kPa-a, preferably, a pressure of 1500 to 4137 kPa-a, a WHSV based on total ethylene and the total amount of catalyst for the overall reactor of 0.1 to 10 hr$^{-1}$, preferably, 0.2 to 2 hr$^{-1}$, more preferably, 0.5 to 1 hr$^{-1}$, or a WHSV based on both total ethylene and total benzene, and the total amount of catalyst for the overall reactor of 10 to 100 hr$^{-1}$, preferably, 20 to 50 hr$^{-1}$, and a molar ratio of benzene to ethylene from about 1 to about 10.

The transalkylation reaction may take place under at least partially in liquid phase conditions. Particular conditions for carrying out the at least partially in liquid phase transalkylation of polyalkylated aromatic compound(s), e.g., polyethylbenzene(s) or polyisopropylbenzene(s), with benzene may include a temperature of from about 100° to about 300° C., a pressure of 696 to 4137 kPa-a, a WHSV based on the weight of the polyalkylated aromatic compound(s) feed to the alkylation reaction zone of from about 0.5 to about 100 hr$^{-1}$ and a molar ratio of benzene to polyalkylated aromatic compound(s) of from 1:1 to 30:1, preferably, 1:1 to 10:1, more preferably, 1:1 to 5:1.

In another embodiment, the transalkylation reaction may take place under vapor phase conditions. Particular conditions for carrying out the vapor phase transalkylation of polyalkylated aromatic compound(s), e.g., polyethylbenzene(s) or polyisopropylbenzene(s), with benzene may include a temperature of from about 350 to about 450° C., a pressure of 696 to 1601 kPa-a, a WHSV based on the weight of the polyalkylated aromatic compound(s) feed to the reaction zone of from about 0.5 to about 20 hr$^{-1}$, preferably, from about 1 to about 10 hr$^{-1}$, and a molar ratio of benzene to polyalkylated aromatic compound(s) of from 1:1 to 5:1, preferably, 2:1 to 3:1.

In some embodiments, this disclosure relates to:

Paragraph 1: A catalyst composition comprising:
(a) a MCM-22 family molecular sieve; and
(b) a binder,
wherein the MCM-22 family molecular sieve is characterized by an average crystal agglomerate size of less than or equal to 16 microns.

Paragraph 2: The catalyst composition of paragraph 1, wherein the average crystal agglomerate size is less than or equal to 15 microns.

Paragraph 3: The catalyst composition of any preceding paragraph, wherein the average crystal agglomerate size is less than or equal to 10 microns.

Paragraph 4: The catalyst composition of any preceding paragraph, wherein the average crystal agglomerate size is less than or equal to 5 microns.

Paragraph 5: The catalyst composition of any preceding paragraph, wherein the average crystal agglomerate size is less than or equal to 2 microns.

Paragraph 6: The catalyst composition of any preceding paragraph wherein the MCM-22 family molecular sieve comprises at least one of MCM-22, MCM-36, MCM-49, MCM-56, ITQ-1, ITQ-30, and any combination thereof.

Paragraph 7: The catalyst composition of any preceding paragraph, wherein the binder comprises at least one of a titanium compound, an alumina compound, a silicon compound, or any mixture thereof.

Paragraph 8: The catalyst composition of any preceding paragraph, wherein the binder is selected from a group consisting of silica, alumina, zirconia, titania, thoria, beryllia, magnesia, silica-alumina, silica-magnesia, silica-zirconia, silica-thoria, silica-beryllia, silica-titania, silica-alumina-thoria, silica-alumina-zirconia, silica-alumina-magnesia, silica-magnesia-zirconia, and any combination thereof.

Paragraph 9: The catalyst composition of any preceding paragraph having at least 50 wt % of the MCM-22 family molecular sieve based on the total weight of the catalyst composition.

Paragraph 10: The catalyst composition of any preceding paragraph further comprising a second molecular sieve having a Constraint Index of less than 12.

Paragraph 11: The catalyst composition of any preceding paragraph further comprising a second molecular sieve having a Constraint Index of less than 2.

Paragraph 12: The catalyst composition of any preceding paragraph wherein the MCM-22 family molecular sieve is made by jet milling to the average crystal agglomerate size.

Paragraph 13: A process for alkylation or transalkylation of an alkylatable aromatic compound with an alkylating agent to produce a monoalkylated aromatic compound, comprising the step of contacting at least one the alkylatable aromatic compound and at least one the alkylating agent with a catalyst composition under suitable alkylation or transalkylation conditions, to produce at least one effluent which comprises the monoalkylated aromatic compound and a monoalkylated aromatic compound selectivity; the catalyst composition comprising:
(i) a MCM-22 family molecular sieve; and
(ii) a binder,
wherein the MCM-22 family molecular sieve is characterized by an average crystal agglomerate size of less than or equal to 16 microns.
wherein the monoalkylated aromatic compound selectivity of the catalyst composition is greater than the monoalkylated aromatic compound selectivity of a catalyst composition having an average crystal agglomerate size greater than 16 microns, when the reaction zone is operated under equivalent conditions.

Paragraph 14: The process of paragraph 13, wherein the average crystal agglomerate size is less than or equal to 15 microns.

Paragraph 15: The process of paragraph 13 or 14, wherein the average crystal agglomerate size is less than or equal to 10 microns.

Paragraph 16: The process of any one of paragraphs 13-15, wherein the catalyst composition further comprises a second molecular sieve having a Constraint Index of less than 12.

Paragraph 17: The process of any one of paragraphs 13-16, wherein the catalyst composition further comprises a second molecular sieve having a Constraint Index of less than 2.

Paragraph 18: The process of any one of paragraphs 13-17, wherein the catalyst composition consists essentially of a MCM-22 family molecular sieve.

Paragraph 19: The process of paragraph 18, wherein the MCM-22 family molecular sieve comprises at least one of ERB-1, ITQ-1, ITQ-2, ITQ-30, PSH-3, SSZ-25, MCM-22, MCM-36, MCM-49, MCM-56, and any combination thereof.

Paragraph 20: The process of paragraph 16, wherein the second molecular sieve comprises a molecular sieve selected from a group consisting of zeolite beta, zeolite Y, Ultrastable Y, Dealuminized Y, rare earth exchanged Y, mordenite, TEA-mordenite, ERB-1, ITQ-1, ITQ-2, ITQ-30, PSH-3, SSZ-25, MCM-22, MCM-36, MCM-49, MCM-56, silicalite, ZSM-3, ZSM-4, ZSM-5, ZSM-11, ZSM-12, ZSM-14, ZSM-18, ZSM-20, ZSM-22, ZSM-23, ZSM-35, and ZSM-48.

Paragraph 21: The process of any one of paragraphs 13-20, further comprising a finishing reactor downstream of the reaction zone.

Paragraph 22: The process of any one of paragraphs 13-21, wherein the suitable alkylation or transalkylation conditions include a temperature from about 100° C. to about 400° C., a pressure from about 20.3 to 4500 kPa-a, a WHSV from about 0.1 to about 10 hr$^{-1}$, and a molar ratio of the alkylatable compound over the alkylating agent from about 0.1:1 to 50:1.

Paragraph 23: The process of any one of paragraphs 13-22, wherein the monoalkylated aromatic compound comprises ethylbenzene, the alkylatable aromatic compound comprises benzene, and the alkylating agent comprises ethylene.

Paragraph 24: The process of any one of paragraphs 13-22, wherein the monoalkylated aromatic compound comprises cumene, the alkylatable aromatic compound comprises benzene, and the alkylating agent comprises propylene.

Paragraph 25: The process of any one of paragraphs 13-24, wherein the monoalkylated aromatic compound selectivity of the catalyst composition is at least 10% greater than the monoalkylated aromatic compound selectivity of a catalyst composition having an average crystal agglomerate size of greater than 16 microns.

Paragraph 26: A process for preparing the catalyst composition of any one of paragraphs 1-12 comprising:
(a) providing the MCM-22 family molecular sieve having an average crystal agglomerate size of less than or equal to 16 microns and the binder to form a mixture; and
(b) forming the mixture into the catalyst composition.

Paragraph 27: The process of paragraph 26, wherein the forming step comprises extruding.

Paragraph 28: The process of any one paragraphs 26-27, wherein the catalyst composition has a shape of quadrulobe.

Paragraph 29: The process of any one paragraphs 26-28, wherein the catalyst composition has at least 65 wt % of crystalline MCM-22 family molecular sieve based on the total weight of the catalyst composition.

Paragraph 30: The process of any one paragraphs 26-29, wherein the catalyst composition further at least 5 wt % of a molecular sieve having a *BEA framework type based on the total weight of the catalyst composition.

Paragraph 31: The process of any one paragraphs 26-30 further comprising a step of jet-milling a MCM-22 family molecular sieve to form the MCM-22 family molecular sieve having an average crystal agglomerate size of less than or equal to 16 microns.

These and other facets of the present invention are exemplified by the following Examples.

Testing Procedures

Feed Pretreatment

Benzene (99.96 wt %) was obtained from the ExxonMobil Baytown Chemical plant. The benzene was passed through a pretreatment vessel (2 Liter Hoke vessel) containing absorbent materials from inlet to outlet. All absorbent feed pretreatment materials were dried in a 260° C. oven for 12 hours before using.

Polymer grade propylene was obtained from Scott Specialty Gases (Pasadena, Tex., USA). Propylene was passed through a 300 ml vessel containing absorbents which were dried in a 260° C. oven for 12 hours before using.

Ultra high purity grade Nitrogen was obtained from Scott Specialty Gases. Nitrogen was passed through a 300 ml vessel containing absorbents which were dried at 260° C. for 12 hours before using.

Alumina was obtained from UOP LLC (UOP LLC, 25 East Algonquin Road, Des Plaines, Ill. 60017-5017, U.S.A.) as Versal-300 alumina.

Catalyst Preparation and Loading

MCM-22 catalyst was prepared according to U.S. Pat. No. 4,954,325, the whole content of which is incorporated herein as reference. MCM-49 catalyst was prepared according to U.S. Pat. No. 5,236,575, the whole content of which is incorporated herein as reference.

Catalyst activity was calculated using the second order rate constant under the reaction conditions (temperature 130° C. and pressure 2170 kPa-a). Reaction rate-constants were calculated using methods known to those skilled in the art. See "Principles and Practice of Heterogeneous Catalyst", J. M. Thomas, W. J. Thomas, VCH, 1st Edition, 1997, the disclosure of which is incorporated herein by reference. Catalyst selectivity was calculated using the weight ratio of cumene produced over di-isopropyl benzenes produced under the reaction conditions (temperature 130° C. and pressure 2170 kPa-a).

One gram of catalyst was dried in air at 260° C. for 2 hours. The catalyst was removed immediately after drying. The bottom of a catalyst basket was packed with quartz chips followed by loading of 0.5 grams of catalyst into basket on top of the quartz chips. The catalyst was then covered by additional quartz chips. The catalyst basket containing the catalyst and quartz chips was dried at 260° C. in air for about 16 hours.

Before each experiment the reactor and all lines were cleaned with a suitable solvent (such as toluene) followed by flowing of air after cleaning to remove all cleaning solvent. The catalyst basket containing the catalyst and quartz chips was placed in reactor immediately after drying.

A 300 ml Parr® batch reaction vessel (Series 4563 mini Bench top reactor with a static catalyst basket, Parr Instrument Company, Moline, Ill. USA) equipped with a stir rod and static catalyst basket was used for the activity and selectivity measurements. The reaction vessel was fitted with two removable vessels for the introduction of benzene and propylene respectively.

The reactor was purged with 100 ml/min of the treated ultra high purity nitrogen, $N_2$, for 2 hours at 170° C. Then, the reactor temperature was reduced to 130° C. under nitrogen flow. All inlets and outlets of the reactor were closed off afterward. Pretreated benzene (156.1 gram) was transferred into the reactor under 791 kPa-a ultra high purity nitrogen blanket. The reactor was stirred at 500 rpm for 1 hour. Pretreated liquid propylene (28.1 gram) under 2170 kPa-a ultra high purity nitrogen is then transferred to the reactor. The reactor was maintained at 2170 kPa-a by the 2170 kPa-a ultra high purity nitrogen. Liquid samples were taken at 15, 30, 60, 120, 180 and 240 min after addition of the propylene.

Jet milling was performed on a Micron Master Jet Mill (Jet Pulverizer, in Moorestown, N.J., USA).

Example 1

Figure 1:
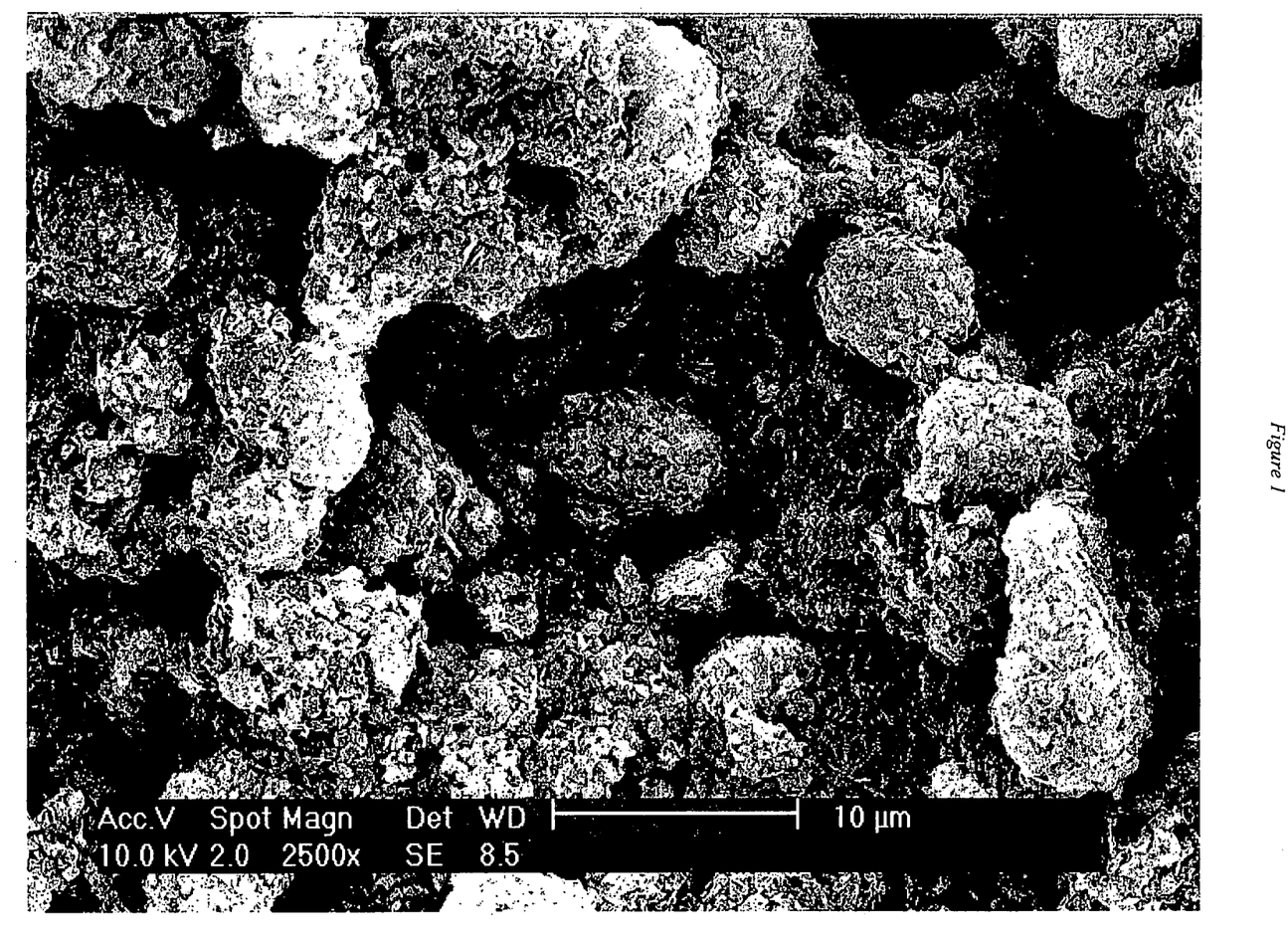
FIG. 1 shows the SEM image of the as-synthesized MCM-49 molecular sieve.

MCM-49 was extruded in a 5.08 cm (2") extruder according to the following formulation: mixture of MCM-49 crystal and Versal-300 alumina (weight ratio 80:20) extruded with 0.05 wt % PVA (based on the combined weight of MCM-49 crystal, Versal-300 alumina, and PVA) to 0.127 cm (1/20") extrudate. This extrudate was then pre-calcined in nitrogen at 510° C., ammonium exchanged with ammonium nitrate, and calcined in an air/N₂ mixture at 538° C. FIG. 1 shows the SEM pictures of the MCM-49 molecular sieve crystal before jet milling. The average crystal agglomerate size is 16.8 microns. The catalyst from Example 1 was tested in the batch autoclave liquid phase benzene alkylation test and results are listed in Table 1.

Example 2

Figure 2:
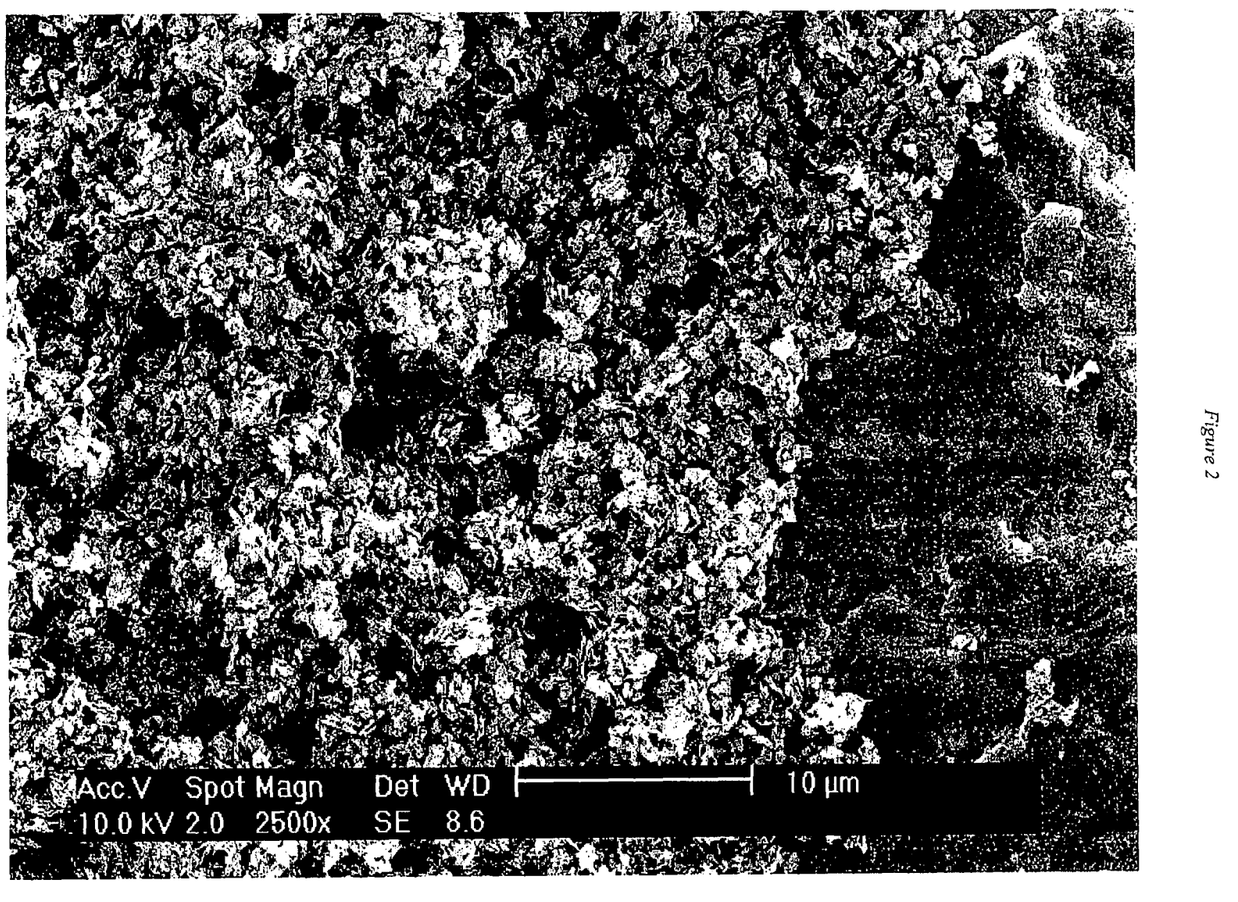
FIG. 2 shows the SEM image of the jet-milled MCM-49 molecular sieve.

MCM-49 was jet pulverized (also called Jet milling) at high velocity mixing. After jet milling, the average crystal agglomerate size of the MCM-49 material decreased from the 16.8 microns to 1.2 microns. The jet milled MCM-49 crystals were extruded in a 5.08 cm (2") extruder according to the following formulation: mixture of MCM-49 crystal and Versal-300 alumina (weight ratio 80:20) extruded with 0.05 wt % PVA (based on the combined weight of MCM-49 crystal, Versal-300 alumina, and PVA) to 0.127 cm (½₀") extrudate. This extrudate was then pre-calcined in nitrogen at 510° C., ammonium exchanged with ammonium nitrate, and calcined in an air/N₂ mixture at 538° C. FIG. 2 shows the SEM pictures of the jet pulverized MCM-49 molecular sieve crystal. The catalyst from Example 2 was tested in the batch autoclave liquid phase benzene alkylation test and results are listed in Table 1.

Table 1 lists the activity and selectivity of catalysts from example 1 and 2. The activity of the example 2 is normalized to the activity of the example 1.

| Example | Activity normalized to example 1 | Cumene Selectivity normalized to example 1 |
|---|---|---|
| Example 1 | 100 | 161 |
| Example 2 | 100 | 100 |

An SEM comparison of the as-synthesized crystal shows large agglomerates of crystals whereas the jet-milled material shows a uniform distribution of much smaller size agglomerate of crystals (see FIG. 1 and FIG. 2).

Decreasing crystal agglomerate size of the MCM-22 family of zeolites dramatically improves the selectivity for liquid phase alkylation of benzene with light olefins. The amount of di-alkylbenzene product is decreased when the crystal agglomerate size is reduced. The examples illustrated the impact of a physical means of reducing crystal agglomerate size.

We claim:

1. A process for alkylation or transalkylation of an alkylatable aromatic compound with an alkylating agent to produce a monoalkylated aromatic compound, comprising the steps of:
   (a) providing crystal agglomerates of a MCM-22 family molecular sieve;
   (b) reducing the size of said crystal agglomerates of said MCM-22 family molecular sieve by chemical or physical means to an average of less than or equal to 2 microns to form reduced-size MCM-22 family molecular sieve agglomerates;
   (c) forming a catalyst composition comprising said reduced size MCM-22 family molecular sieve agglomerates and a binder, said catalyst composition having a monoalkylated aromatic compound selectivity; and
   (d) contacting at least one alkylatable aromatic compound and at least one alkylating agent with said catalyst composition under suitable alkylation or transalkylation conditions, to produce at least one effluent which comprises said monoalkylated aromatic compound;
   wherein the monoalkylated aromatic compound selectivity of said catalyst composition is greater than the monoalkylated aromatic compound selectivity of a catalyst composition having an average crystal agglomerate size greater than 16 microns, when said reaction zone is operated under equivalent conditions.

2. The process of claim 1, wherein said catalyst composition further comprises a medium pore molecular sieve having a Constraint Index of 2-12.

3. The process of claim 1, wherein said catalyst composition further comprises a large pore molecular sieve having a Constraint Index of less than 2.

4. The process of claim 1, wherein said catalyst composition consists essentially of said reduced-sized MCM-22 family molecular sieve agglomerates.

5. The process of claim 1, wherein said MCM-22 family molecular sieve comprises at least one of ERB-1, ITQ-1, ITQ-2, ITQ-30, PSH-3, SSZ-25, MCM-22, MCM-36, MCM-49, MCM-56, and any intergrowth-phase thereof or mix phase thereof.

6. The process of claim 2, wherein said medium pore molecular sieve is selected from a group consisting of silicalite, ZSM-5, ZSM-11, ZSM-12, ZSM-22, ZSM-23, ZSM-35, and ZSM-48.

7. The process of claim 1, wherein said suitable alkylation or transalkylation conditions include a temperature from about 100° C. to about 400° C., a pressure from about 20.3 to 4500 kPa-a, a WHSV from about 0.1 to about 10 hr$^{-1}$, and a molar ratio of said alkylatable compound over said alkylating agent from about 0.1:1 to 50:1.

8. The process of claim 1, wherein said monoalkylated aromatic compound comprises ethylbenzene, said alkylatable aromatic compound comprises benzene, and said alkylating agent comprises ethylene.

9. The process of claim 1, wherein said monoalkylated aromatic compound comprises cumene, said alkylatable aromatic compound comprises benzene, and said alkylating agent comprises propylene.

10. The process of claim 1, wherein the monoalkylated aromatic compound selectivity of said catalyst composition is at least 10% greater than the monoalkylated aromatic compound selectivity of a catalyst composition having an average crystal agglomerate size of greater than 16 microns.

11. The process of claim 1, wherein said physical means for reducing the size of said crystal agglomerates of reducing step (b) is selected from the group consisting of crushing, milling, grinding, jet-milling, slurry/spray drying, pressing mixing and any combination thereof.

12. The process of claim 1, wherein said MCM-22 family molecular sieve is characterized by having an X-ray diffraction pattern including d-spacing maxima at 12.4±0.25, 3.57±0.07 and 3.42±0.07 Angstroms either calcined or as-synthesized.

13. The process of claim 3, wherein said large pore molecular sieve is selected from the group consisting of zeolite beta, zeolite Y, Ultrastable Y, Dealuminized Y, rare earth exchanged Y, mordenite, TEA-mordenite, ZSM-3, ZSM-4, ZSM-18 and ZSM-20.

* * * * *